United States Patent [19]

Komine et al.

[11] Patent Number: 4,458,233

[45] Date of Patent: Jul. 3, 1984

[54] GAS SENSING ELEMENT

[75] Inventors: Yoshiharu Komine; Takao Sawada, both of Amagasaki, Japan

[73] Assignee: Mitsubishi Denki Kabushiki Kaisha, Tokyo, Japan

[21] Appl. No.: 475,972

[22] Filed: Mar. 16, 1983

[30] Foreign Application Priority Data

Mar. 30, 1982 [JP] Japan ................................ 57-51852
Mar. 30, 1982 [JP] Japan ................................ 57-51853

[51] Int. Cl.$^3$ ............................................. H01L 7/00
[52] U.S. Cl. ......................................... 338/34; 422/98; 422/94
[58] Field of Search ...................... 338/34; 422/95, 98, 422/94, 90; 204/292, 295, 296

[56] References Cited

U.S. PATENT DOCUMENTS

| | | | |
|---|---|---|---|
| 3,479,257 | 11/1969 | Shaver | 338/34 X |
| 4,146,438 | 3/1979 | de Naro et al. | 204/242 X |
| 4,224,280 | 9/1980 | Takahama et al. | 338/34 X |
| 4,260,978 | 4/1981 | Yasuda et al. | 338/34 |
| 4,272,353 | 6/1981 | Lawrence et al. | 204/296 X |
| 4,326,414 | 4/1982 | Teranda et al. | 338/35 X |

OTHER PUBLICATIONS

Journal of Electronic Materials, vol. 10, No. 3, 1981 R. B. Cooper et al., "Gas Sensing Mechanisms in $SnO_2$ Thin Films".

Primary Examiner—Roy N. Envall, Jr.
Assistant Examiner—Christopher N. Sears
Attorney, Agent, or Firm—Oblon, Fisher, Spivak, McClelland & Maier

[57] ABSTRACT

A gas sensing element made of a gas sensing material composed of a composite oxide of titanium and niobium as the principal constituent, which is capable of measuring with high sensitivity and selectivity those gases such as hydrogen sulfide, methyl mercaptan, etc. issuing offensive odor, and alcohol, due to variations in electrical resistance of the material.

2 Claims, 6 Drawing Figures

GAS SENSING ELEMENT

BACKGROUND OF THE INVENTION

1. Field of the Invention

This invention relates to a gas sensing element to detect alcoholic gas and those gases giving off an offensive odor such as, for example, methyl mercaptan ($CH_3SH$), hydrogen sulfide ($H_2S$), and so forth.

2. Description of Prior Art

Concentration measurement of methyl mercaptan, hydrogen sulfide, and other gases which are the principal components of offensive odor emitted from sewage disposing sites, refuse disposing sites, etc. has been done partly in an electro-chemical process. For this purpose, however, sampling of such gases is necessary and procedures for the measurement are also complicated. On the other hand, the conventional semiconductor gas sensor is still not satisfactory in its sensing capability and has not yet found its way into practical use.

As an element to detect inflammable gases, i.e., a gas sensing element, there have been known various types to be mentioned as follows: (a) an element which utilizes variations in electrical conductivity of a material constituting the same due to chemical adsorption of the gases; (b) an element which detects a rise in its temperature due to burning of the inflammable gas which has come into contact with the element; (c) an element which utilizes a gas concentration dependent property of an electromotive force of a solid electrolyte; (d) an element which utilizes a gas concentration dependent property of infrared ray absorption intensity; and others. Of these various types of gas sensing element, the type (a) of the element has been mainly employed for the purpose of continuous measurements or controls of the gases owing to its convenience in use, stability in its operation, heat-resistant property, and so forth. More specifically, this type of gas sensing element utilizes variations in the electrical conductivity of a metal oxide ceramic semi-conductor due to its chemical adsorption of a gas. For the metal oxide to be the base material for the sensing element, there have been mostly used $SnO_2$, $ZnO$, etc. as the principal component. While these metal oxides are sensitive to inflammable gases such as methane, propane, hydrogen, carbon monoxide, alcohol, and so on, they have disadvantageously poor selectivity to alcohol. As a matter of fact, it has happened not infrequently that a gas leakage sensor (or a gas alarm) has given off a warning signal even by alcohol vapor from wine while it is being warmed for 'hot wine'.

SUMMARY OF THE INVENTION

It is an object of the present invention to provide a gas sensing element which is highly sensitive to methyl mercaptan ($CH_3SH$), hydrogen sulfide ($H_2S$), and other gases having offensive odor, and has a selectively high sensitivity to alcohol, i.e., a particular sensitivity to alcohol which is different from the sensitivity to other inflammable gases.

It is another object of the present invention to provide a gas sensing element made of a gas sensing material consisting of a composite oxide of titanium and niobium, with which ruthenium oxide is mixed, or a gas sensing element comprising a base plate for the element made of a composite oxide of titanium and niobium as the principal component, on which an electrode made of ruthenium oxide as the principal component has been baked, thereby promoting increased sensitivity to foul-smelling gases as well as alcohol gas.

It is still another object of the present invention to provide a gas sensing element capable of readily detecting foul-smelling gases or alcohol gas by measuring electric resistance values of the element, based on the fact that, when the gas sensing material according to the present invention is used, its electrical resistance value changes remarkably at a concentration of the bad smell gases and alcohol gas in a range of from 0 to 3,000 ppm. Further, this gas sensing element is substantially insensitive to those inflammable gases such as methane, ethane, propane, hydrogen, carbon monoxide, etc., except for alcohol, so that its selective sensitivity to alcohol improves remarkably in comparison with the conventional alcohol sensor.

According to the present invention, in one aspect of it, there is provided a gas sensing element made up of a gas sensing material consisting of a composite oxide of titanium and niobium as the principal constituent.

According to the present invention, in another aspect of it, there is provided a gas sensing element made up of a gas sensing material consisting of a composite oxide of titanium and niobium, with which ruthenium oxide is mixed.

According to the present invention, in still another aspect of it, there is provided a gas sensing element comprising a base plate for the element consisting of a composite oxide of titanium and niobium as the principal constituent, on which an electrode made of ruthenium oxide as the principal component is baked.

The foregoing objects, other objects as well as specific construction and function of the gas sensing element according to the present invention will become more apparent and understandable from the following detailed description of it, when read in connection with the accompanying drawing.

BRIEF DESCRIPTION OF THE ACCOMPANYING DRAWING

DESCRIPTION OF PREFERRED EMBODIMENTS

In the following, the present invention will be described in detail with reference to a few preferred examples thereof and in reference to the accompanying drawing.

EXAMPLE 1

As the starting material, titanium oxide $TiO_2$ and niobium oxide $Nb_2O_5$, both being graded as high purity reagents, were mixed at seven kinds of mixing ratios, i.e., Ti:Nb=6:1, 4:1, 2:1, 1:1, 1:2, 1:4, and 1:6. The mixed material in these different mixing ratios was formed under a pressure to a dimension of 6 mm long, 6 mm wide, and 1 mm thick. The obtained specimens were sintered for two hours at a temperature range of from 1,000° to 1,400° C. When the specimens as sintered were subjected to identification under the X-ray diffraction, the results as shown in the following Table were obtained.

TABLE

| Ti:Nb | 1,000° C., 2 hrs. | 1,200° C., 2 hrs. | 1,300° C., 2 hrs. | 1,400° C., 2 hrs. |
|---|---|---|---|---|
| 6:1 | $TiO_2$ | $TiO_2$ | $TiO_2$ | $TiO_2$ |
| 4:1 | $TiO_2$ | $TiO_2$ | $TiO_2$ | $TiO_2$ |
| 2:1 | $TiO_2$ + $Ti_2Nb_{10}O_{29}$ | $TiO_2$ + new substance | $TiO_2$ + new substance | $TiO_2$ + new substance |
| 1:1 | $TiO_2$ + $Ti_2Nb_{10}O_{29}$ | $TiO_2$ + new substance + $Ti_2Nb_{10}O_{29}$ | $TiO_2$ + new substance | $TiO_2$ + new substance |
| 1:2 | $TiO_2$ + $Ti_2Nb_{10}O_{29}$ | new substance + $Ti_2Nb_{10}O_{29}$ | new substance | new substance |
| 1:4 | $Ti_2Nb_{10}O_{29}$ + $TiO_2$ | $Ti_2Nb_{10}O_{29}$ + $TiO_2$ | $Ti_2Nb_{10}O_{29}$ − new substance | $Ti_2Nb_{10}O_{29}$ + new substance |
| 1:6 | $Ti_2Nb_{10}O_{29}$ + $Nb_2O_5$ | $Ti_2Nb_{10}O_{29}$ + $Nb_2O_5$ | $Ti_2Nb_{10}O_{29}$ + $Nb_2O_5$ | $Ti_2Nb_{10}O_{29}$ + $Nb_2O_5$ |

Figure 1:
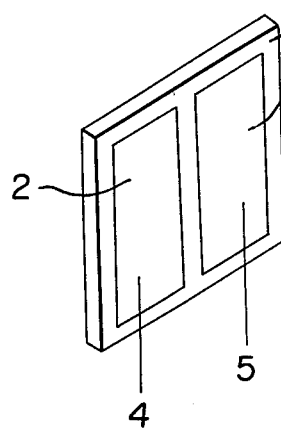
FIG. 1 is a perspective view showing a general construction of one embodiment of the gas sensing element according to the present invention.

The above identifications were obtained on the basis of the ASTM Designation. In the above Table, those substances which could not be identified by the ASTM Designation were termed "new substances". These new substances were, however, a composite oxide of titanium and niobium which could be recognized as having niobium and titanium in a range of $\frac{1}{2} \leq Nb/Ti \leq 4/1$. When these sintered substances were polished to a thickness of 300 microns, it was found that the specimens composed of Ti:Nb=6:1, 4:1, 1:4, and 1:6 and sintered at 1,000° C. were subjected to breakage, while the specimens composed of Ti:Nb=2:1, 1:1, and 1:2 and sintered at 1,000° C. and 1,200° C. were subjected to breakage. Then, the remaining specimens not subjected to breakage were fabricated into the gas sensing elements by attaching separate electrodes 2, 3 made of $RuO_2$ and lead wires 4, 5 to one surface of the sintered body 1 as shown in FIG. 1, followed by examination of their gas sensitivity characteristics. The sintered body 1 is made of a composite oxide of titanium and niobium. When detecting gas, the element should be maintained at a temperature of 300° C. or higher. For this purpose, a coil heater made of tantalum wire is provided around the element in FIG. 1, or a planar heater is attached onto the other surface of the sintered body 1 in FIG. 1 opposite to the separate electrodes, thereby heating the sintered body.

Figure 2:
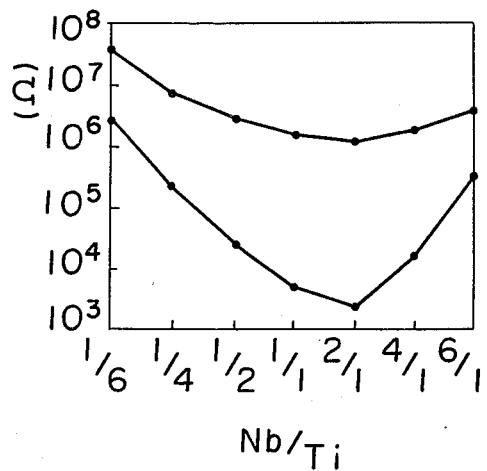
FIGS. 2 and 3 are graphical representations of characteristic polygonal lines showing the composition-dependent property of the gas sensing characteristic of the gas sensing material according to the present invention.

FIG. 2 indicates the gas sensitivity characteristic of the gas sensing element at an element temperature of 450° C. and concentration of methyl mercaptan gas of 100 ppm in terms of a relationship between the mixing ratio of Nb and Ti and an electrical resistance value ($\Omega$). In the graphical representation, the electrical resistance values in air are meant by those in ordinary air not containing methyl mercaptan.

The graph shows the gas sensing characteristic of the element fabricated at a low sintering temperature. As the sintering temperature increases, the sensitivity lowers. With the mixing ratio of Nb/Ti being $0.5 \leq Nb/Ti \leq 4$, the sensitivity of the element to methyl mercaptan becomes large, and the electrical resistance in the air decreases. This range of the mixing ratio coincides with the range of presence of the "new substance", which is considered to be contributory to the high sensitivity. The most preferred ratio of mixing between niobium and titanium is Nb/Ti=2/1, in which case presence of $TiO_2$, $Nb_2O_5$, and $Ti_2Nb_{10}O_{29}$ cannot be ascertained even through the X-ray diffraction.

When a ratio between the electrical resistance value Ra in the air and the electrical resistance value Rg in a gas concentration of 100 ppm (Ra/Rg) is set to be a sensitivity S, this sensitivity value reaches 500 times with Nb/Ti=2/1.

Figure 3:
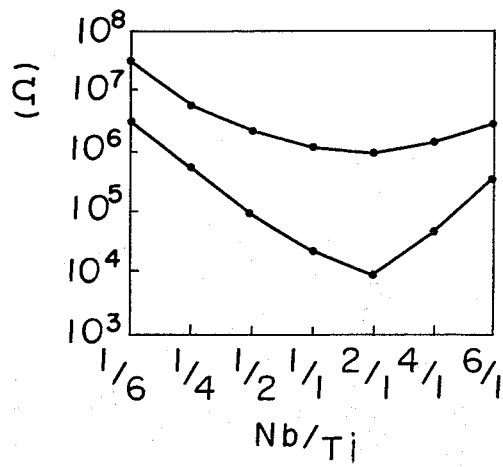

FIG. 3 shows the sensitivity characteristic to ethanol of the element at an element temperature of 450° C. in terms of a relationship between the mixing ratio of Nb and Ti and the electrical resistance value ($\Omega$). This characteristic is shown in comparison with the resistance value in the air and that in the ethanol concentration of 1,000 ppm.

The graph shows the gas sensing characteristic of the element fabricated at a low sintering temperature. As the sintering temperature increases, the sensitivity lowers.

Within the range of presence of the new substance, the sensing element exhibits an extremely high sensitivity, although, even in the range where the new substance is not present, variations in the resistance value is ten times as high as that in the air, hence its sensitivity to alcohol is high. Incidentally, the sensitivity to alcohol of the conventional gas sensing element ranges from two to three times.

Figure 4:
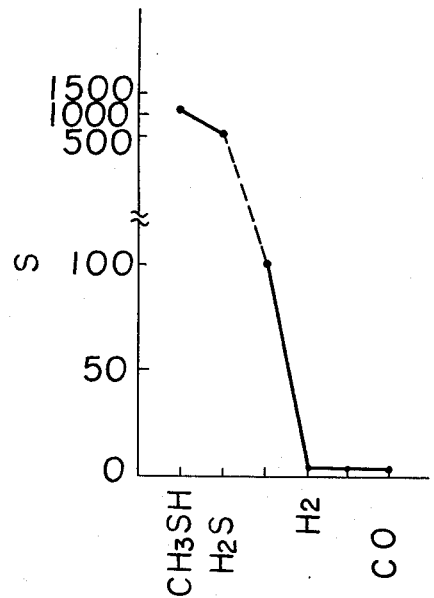
FIG. 4 is also a graphical representation of the characteristic polygonal line showing the sensitivity to various gases of the gas sensing element according to the present invention.

FIG. 4 indicates the sensitivity S of the gas sensing element to propane, hydrogen, carbon monoxide, ethanol, methyl mercaptan, and hydrogen sulfide at a gas concentration of 1,000 ppm, the sensitivity being shown in terms of a ratio (Ra/Rg) between the electrical resistance value Ra in the air and the electrical resistance value Rg in the gas concentration of 1,000 ppm. The operating temperature of the element is 450° C. and the mixing ratio of Nb and Ti is 2:1. When the mixing ratio of Nb and Ti is varied in a range of from 1:6 to 6:1, the abovementioned ratio Ra/Rg changed in a range of from 100 to 10.

As seen from FIG. 4, the gas sensing element has no substantial sensitivity to propane, hydrogen and carbon monoxide. The element showed a sensitivity to methanol and isopropyl alcohol as substantially equal a degree as to ethanol.

The response of the gas sensing element to methyl mercaptan and alcohol is approximately four seconds with the gas density range of from zero to 100 ppm, which is extremely fast. Substantially no change in the sensing characteristic could be recognized after continuous voltage application for a six-month period.

EXAMPLE 2

As the starting material, titanium oxide $TiO_2$ and niobium oxide $Nb_2O_5$, both being graded as high purity reagents, were mixed at a mixing ratio of $Nb/Ti=2:1$, and then the mixture was sintered in the air for one hour at 1,200° C. The sintered material was then pulverized, and then the pulverized material was passed through a 100-mesh sieve. Thereafter, the powdered material was mixed with powder of ruthenium oxide $RuO_2$ with the content of $RuO_2$ being changed in a range of from zero to 50 wt.%. To this mixture, polyvinyl alcohol was added as a binder to be pelletized. The pelletized material was subjected to shaping under pressure having a dimension of 6 mm long, 6 mm wide, and 1 mm thick. The shaped article was sintered in the air for two hours at a temperature of 1,300° C. The resulted sintered body 1 was polished to a thickness of 300 microns, on one surface of which the separated electrodes 2, 3 made of paste of $RuO_2$ was screenprinted at a space interval therebetween of 500 microns, as shown in FIG. 1, and then the platinum lead wires 4, 5 were attached to the electrodes with the $RuO_2$ paste, followed by baking the same for 10 minutes at 800° C.

The sintered body 1 is a ceramic composition consisting of the composite oxide of titanium and niobium, to which ruthenium oxide is added to constitutes the gas sensing material of the present invention. It should be noted incidentally that, even if the content of ruthenium oxide is nil, paste of ruthenium oxide ($RuO_2$) containing therein $RuO_2$ as the principal constituent is attached, as the electrodes, onto the gas sensing material consisting of the composite oxide of titanium and niobium, i.e., the element base, and fixed thereon by baking.

Figure 5:
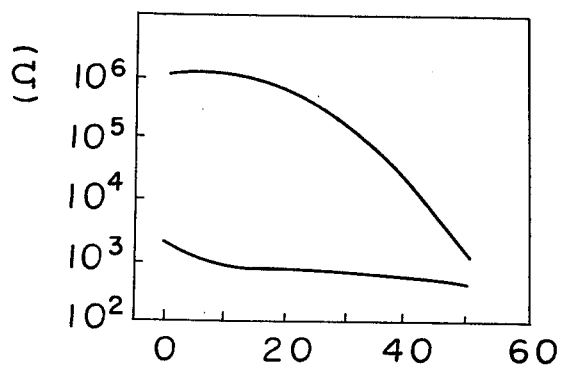
FIG. 5 is a characteristic curve showing the composition-dependent property of the gas sensing characteristic of the gas sensing material according to the present invention.

FIG. 5 shows a relationship between the content or $RuO_2$ and the electrical resistance. As shown in this graphical representation, even when the content of ruthenium oxide is nil in the gas sensing material, those elements, onto which the electrodes made of $RuO_2$ as the principal component is attached and baked, or those elements, in which ruthenium oxide is incorporated later, exhibit remarkable variation in its resistance value at the concentration of methyl mercaptan of 100 ppm. Again, even if the content of $RuO_2$ is nil in the gas sensing material, those elements, to which the electrodes made of $RuO_2$ as the principal constituent were attached and baked, or those elements, in which $RuO_2$ has been incorporated in the gas sensing material later at a ratio of from zero to 40 wt.%, indicate remarkable variation in the resistance value, which is practical. In particular, those elements, to which the electrodes made of ruthenium oxide as the principal component are attached and baked, or those elements, in which ruthenium oxide is incorporated into the gas sensing material later at a ratio of from 5 to 25 wt.% exhibit remarkably large change in the resistance value. However, when the content of $RuO_2$ is in a range of from 40 to 50 wt.%, the resistance value of the element in the air lowers remarkably, variations in its resistance value becomes small, and the sensitivity thereof becomes also inferior.

Figure 6:
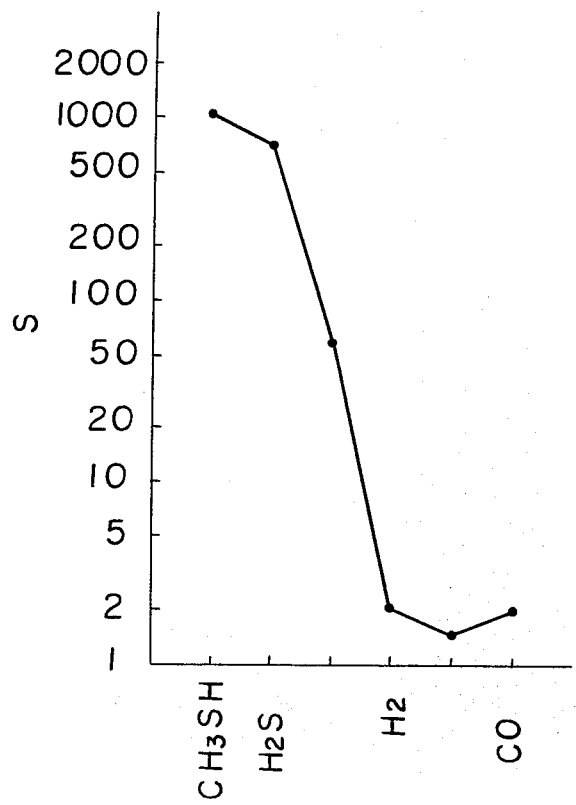
FIG. 6 is a graphical representation of the characteristic polygonal line showing the sensitivity characteristic to various kinds of gas of the gas sensing element according to the present invention.

FIG. 6 indicates the sensitivity S at the concentration of the bad smell gas and the inflammable gas of 100 ppm of the gas sensing element made of a gas sensing material consisting of the composite oxide of titanium and niobium ($Nb/Ti=2$), to which 10% by weight of ruthenium oxide $RuO_2$ is added, and then the electrodes made of $RuO_2$ as the principal constituent are attached to the element and baked.

As seen from this graphical representation, the gas sensing element exhibits an extremely low sensitivity to propane, hydrogen, and carbon monoxide, but it exhibits remarkable sensitivity to bad smell gases and ethanol.

Since the values of the electrical resistance are obtained by measuring them at an extremely narrow gap between the electrodes 2, 3 (in this embodiment, it is 500 microns), when the content of $RuO_2$ in the gas sensing material is taken as a problem, a very small portion of the as sensing material in the abovementioned narrow space interval or in its vicinity should be taken as an object of consideration.

Furthermore, the graphical representation in FIG. 1 is concerned with the gas sensing element in a planar form. It should, however, be noted that those gas sensing elements in bead form same as a thermistor, in cylindrical form, or those elements fabricated by printing a material consisting of the composite oxide of titanium and niobium as the principal constituent onto an alumina base in a heavy film thickness, or those elements formed in a thin film thickness, have the same function as the gas sensing element in the planar form.

Thus, in the foregoing, the present invention has been described with particular reference to the preferred examples thereof. However, the invention is not limited to these embodiments alone, but any changes and modifications may be made within the spirit and scope of the present invention as set forth in the appended claims.

We claim:

1. A gas sensing element consisting essentially of a gas sensing material which comprises a mixture of a composite oxide of titanium and niobium, and a ruthenium oxide.

2. A gas sensing element comprising an element base plate made of a mixture of a composite oxide of titanium and niobium, and ruthenium oxide as the principal constituent, and electrodes made of ruthenium oxide as the principal constituent, which is attached and baked to said element base plate.

* * * * *